United States Patent [19]
Del Mar et al.

[11] Patent Number: 6,117,077
[45] Date of Patent: Sep. 12, 2000

[54] LONG-TERM, AMBULATORY PHYSIOLOGICAL RECORDER

[75] Inventors: Bruce Eugene Del Mar, Laguna Beach; Raphael Henkin, Monarch Beach; John A. Bachman, Dana Point, all of Calif.

[73] Assignee: Del Mar Medical Systems, LLC, Irvine, Calif.

[21] Appl. No.: 09/235,658

[22] Filed: Jan. 22, 1999

[51] Int. Cl.[7] .................................. A61B 5/00; A61B 5/04
[52] U.S. Cl. .................. 600/301; 600/300; 600/372; 600/382; 600/386; 600/387
[58] Field of Search ................... 600/300, 301, 600/508, 509, 372, 382, 386, 387; 340/573

[56] References Cited

U.S. PATENT DOCUMENTS

| | | |
|---|---|---|
| 3,215,136 | 11/1965 | Holter . |
| 4,121,573 | 10/1978 | Crovella et al. .................. 600/382 |
| 4,123,785 | 10/1978 | Cherry . |
| 4,532,934 | 8/1985 | Kelen . |
| 4,809,705 | 3/1989 | Ascher ..................................... 600/523 |
| 4,858,617 | 8/1989 | Sanders ................................... 600/509 |
| 5,109,862 | 5/1992 | Kelen . |
| 5,205,295 | 4/1993 | Del Mar . |
| 5,483,967 | 1/1996 | Ohtake .................................... 600/508 |
| 5,634,468 | 6/1997 | Platt et al. .............................. 600/509 |
| 5,724,025 | 3/1998 | Tavori .................................... 340/573 |
| 5,976,083 | 11/1999 | Rchardson et al. ...................... 600/300 |

*Primary Examiner*—Cary O'Connor
*Assistant Examiner*—Navin Natnithithadha
*Attorney, Agent, or Firm*—W. D. English, III

[57] ABSTRACT

A self contained, compact, long term, ambulatory physiological recorder is designed for mounting directly to the body of a patient, immediately adjacent to the organ or system that is to be monitored, and is adhesively and covertly held there in place and comfortably under clothing by the very transducer, skin electrodes that detect the physiological information to be recorded, and thereby increasing continuity and decreasing artifact by obviating the need for numerous and cumbersome, hanging electrode leads as well as unsightly and cumbersome recorder pouches suspended from shoulder straps or belts.

19 Claims, 9 Drawing Sheets

LONG-TERM, AMBULATORY PHYSIOLOGICAL RECORDER

BACKGROUND OF THE INVENTION

1. Field of the Invention

Generally speaking, the invention relates to apparatus and processes for long term, ambulatory monitoring and accumulation of human physiological data. More specifically, the invention disclosed herein consists of a miniature, solid state recorder for ambulatory monitoring of body signals over extended periods of time, sealed against moisture and mounted under all clothing, and supported on a bridge between at least two adhesively attached sensor electrodes in conductive contact with the skin. Provision for direct mounting of the solid state recorder is made possible by the recorder's light weight and flexible structure, and by recent advances in the manufacture of very small memory chips and subminiature solid state, lightweight processor chips incorporated in the invention. The invention not only provides for recording and storing physiological data, but also provides the sensor data input mounts as well as a data output terminal to transfer stored information to a data processing and display unit.

2. Description of the Prior Art

Many and varied long term ambulatory monitoring devices and systems have been developed and marketed over the years with numerous improvements made by applicant herein; most dealing with improved means to provide to the physician a higher and higher accuracy in the assessment of a patient's risk of sudden death from arrhythmia and other life threatening signal abnormalities. The monitoring process, as applied to electrocardiography, was named after its inventor and pioneer research physicist, Norman J. Holter, President of the Holter Research Foundation of Helena, Montana. Holter's coinventor and technical assistant on the original Holter concept was Wilford R. Glasscock. The original Holter concept and invention was assigned to Del Mar Engineering Laboratories of Los Angeles, Calif., under technology license from the Holter Research Foundation dated Apr. 19, 1962, and was filed in the US Patent and Trademark Office by assignee, Del Mar, on Jul. 6, 1962. The application issued as U.S. Pat. No. 3,215,136 on Nov. 2, 1965 and taught not only a long term, ambulatory ECG recording technique but also Holter's data reduction and presentation format promoted under Del Mar's US registered trademarks Electrocardiocorder®, AVSEP®, and Arrhythmiagraph®. The 136 patent specifically taught a means for processing electrocardiographic signals and more particularly to a means for obtaining large quantities of electrocardiac signals and to a means for facilitating the processing and observing in graphic form of large volumes of such signals in a short interval of time.

Based on the presentations set forth in the foregoing 136 Holter patent, Del Mar Engineering Laboratories produced for clinical cardiology the first complete Holter Monitoring Systems in 1963 which immediately inspired research activity of pioneer research cardiologists: Dr. Eliot Corday, Dr. Lawrence E. Hinkle, Dr. Herman K. Hellerstein and Dr. John S. Gilson. As a result of several years of clinical testing by these physicians of the Holter Monitoring procedure resulting in numerous publications in medical journals on results emanating from test on hundreds of patients, Holter Monitoring was endorsed and recommended as a new revelation in cardiovascular clinical practice, and was eventually adopted as a standard practice worldwide.

Since 1965, a progression of Holter improvement patents have issued over the years, notably that of Oct. 31, 1978, U.S. Pat. No. 4,123,785, "Recorder for Cardiac Signals with Manually Activated Event Marker" by inventors Issac R. Cherry and Donald L. Anderson of Del Mar Avionics, successor to Del Mar Engineering Labs. The 785 patent disclosed a small, hip/side mounted tape recorder for ambulatory recording of cardiac signals over a twenty-four hour interval and included a clock with visual display and a patient event marker. Cardiac signals are simultaneously recorded on two tracks on magnetic tape wherein the event marker function could also be recorded and activated by the patient to denote the happening of a specific event sensed by the patient that can be easily recognized on play back in relation to heart activity at the time. The 785 Cherry et al. patent was followed by yet many other noteworthy inventions.

The forgoing US patents taught many important developments in Holter Monitoring technology but were yet followed by a series of other prior patents of Del Mar Avionics dealing with Holter Monitoring concepts. U.S. Pat. No. 4,532,934, was issued August 1985, titled "Pacemaker Monitoring Recorder and Malfunction Analyzer", by inventor George J. Kelen, M.D. The Kelen 934 patent disclosed a hip/side mounted magnetic tape recorder which detects and records sequential pacemaker spikes in one channel in a waveform compatible with corresponding ECG signals recorded in a second tape channel. The system further includes an analysis module connected to the playback unit for receiving both the ECG and pacer spike signals and is adapted to play back both channels of information at 120 times recording speed. An analysis module in the recorder has counters to accumulate the number of paced beats and fusion beats. The system is further configured to sense malfunctions, failure to sense, failure to capture, and abnormal bradycardia.

U.S. Pat. No. 5,109,862 issued May 8, 1992 and was titled "Method and Apparatus for Spectral Analysis of Electrocardiographic Signals," by inventors George J. Kelen, M.D. and Raphael Henkin, Ph.D. The Kelen 862 patent discloses a signal processing and analysis method and apparatus for plotting and measuring ECG signals where the graphic plots and numeric parameters measured reveal abnormalities of electrical conduction within the heart thought to anticipate abnormal heart rhythm, arrhythmia. The invention employs Fourier analysis of short overlapping segments of ECG signal to create a three dimensional electrocardiogram map.

U.S. Pat. No. 5,205,295, issued Apr. 27, 1993 "Method and Apparatus for Holter Recorder with High Resolution Signal Averaging Capability for Late Potential Analysis," by inventors Bruce Del Mar and Isaac R. Cherry. The Del Mar 295 patent discloses a method for digital signal averaging of selected signals and storing for future playback. The averaged signals, several times per hour in a 24 hour period, are correlated with previously defined correlation coefficients to yield summated results that have eliminated nonrepetitive noise. Information so accumulated enable micropotential analysis of cardiac electrical activity.

Since 1996 digital data storage capacity in lightweight disc drives and printed circuit card, flash memory components has progressed in production to the point where solid-state ambulatory physiological recorders can be made at reasonable cost. They offer an advantage over ambulatory physiological tape recorders having no moving parts and no need for separate analog-to-digital data conversion. Solid-state recording now represents a formidable improvement in the art of ambulatory physiological recording.

Long-term ambulatory physiological and Holter recorders have been conventionally worn in a protective pouch slung by straps over the shoulder outside the clothing or hung on a person's belt, again outside the clothing. Many problems and inconveniences can occur while wearing such conventional ambulatory physiological recorders, especially because of the necessary prolonged, continuous recording times involved. Dressing and sleeping become troublesome because of the long wire harness required on existing recorders. Electrodes often get pulled off the chest by the wire harness during sleep and active physical activities. The recorder may also receive rough treatment from dropping to the floor or exposure to other hostile environments. With the invention disclosed herein, compactness and simplicity replace a variety of components and complication. With the new invention disclosed herein, exercise, including walking and running, is unrestricted. The daily routine of sleeping, dressing and bathing need not change! And, for the clinician, this invention can create more reliable long-term monitoring of physiological signal.

SUMMARY OF THE INVENTION

As will be more particularly described herein, the ambulatory data recorder of this invention utilizes compact, contiguous, and high continuity integrated circuitry; A-to-D converters; a CPU operating system; a body/sensor attached and supported system; printed circuit, flash memory and DC power to record one, or more, channels of physiological signal with optional event marking and optional activity monitoring, as well as means to program specific periods of recording with or without data compression. The recorder is provided with at least two adhesive body sensor chest attachments that not only support the recorder housing but also concomitantly sense cardiac or other body activity; the recorder system may, however, have multiple sensor attachments as well and serial or parallel porting to download recorded data for digital analysis and display of a full disclosure or summary data report on a conventional personal computer (PC) or other digital retrieval system. In the preferred embodiment, there are at least three sensor attachments mounted in a triangular manner supporting the CPU recorder therebetween.

OBJECTS OF THE INVENTION

It is a primary object of the invention to provide for a long term, ambulatory physiological data recorder design to obtain more complete and reliable ambulatory physiological recordings by providing a self contained recorder device without electrical leads for mounting on the patient's skin directly adjacent the organ or system to be monitored.

It is yet another substantial object of the invention to enable a physician to attach a compact recorder system to a patient in an environment that is more convenient and comfortable to wear. Higher electrical continuity and more convenient and comfortable recorder attachment and support objects of the invention are made possible by the simplicity of wearing this novel recorder at the signal source and avoiding recording failures or introduction of artifact attributed to loose rigging of the apparatus on the body;

Yet another object of the invention is the provision for recording ambulatory physiological signals in an unseen, covert fashion;

Still another object is to provide ambulatory physiological recording means and processes without the need to change patient's daily routine;

Another object is to provide ambulatory physiological recording without restriction to daily exercise or position of the body or limbs, including walking and running;

Yet another object is to reduce the cost of obtaining ambulatory physiological recordings for the patient, the medical practitioner, and the government;

Still another object of the invention is to provide an ambulatory physiological recording system wherein body activity sensors located directly within the recorder can provide information on body orientation and acceleration simultaneously with other sensor data to measure the relationship between physical activity and sensor data throughout the recording period;

Another object is to provide an ambulatory physiological recorder that is pliable and comfortable to wear by having flexibility to fit the contours of the body across electrode sensor locations;

Yet another object is to provide a readily available ambulatory physiological recorder for short-term recording of body signals while undergoing an informal treadmill or improvised stress test using a limited number of sensors. The period of recording may be short, but the data analysis can be reported quickly from the digital writeout device, already available for other related purposes. Such a stress test can be conducted in the physician's office as an adjunct to other long-term physiological monitoring tests.

DETAILED DESCRIPTION OF A PREFERRED EMBODIMENT

Figure 1:
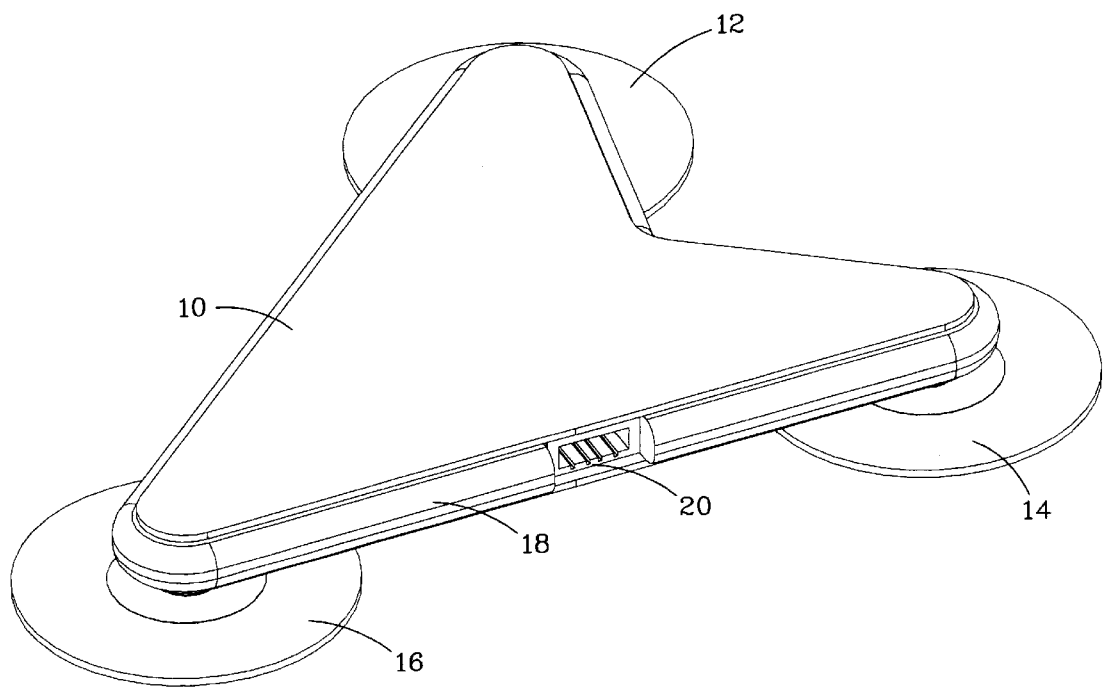
FIG. 1 illustrates a perspective view of a first embodiment of the ambulatory physiological recorder invention.

Although the following description of a preferred embodiment will describe a specific embodiment of the invention concept, it will be appreciated that the scope of the invention concept extends to many obvious and similar other embodiments and will be limited by the breadth of the claims alone and not by the description of the preferred embodiment herein. Only when there is an ambiguity of the terms or meaning of a claim as drafted will the description be necessary to interpret the claims. It will be further understood that like numerals on different figures of the Drawing refer to the same element on each figure.

First Embodiment

A perspective view of a first embodiment of the invention is clearly illustrated in FIG. 1 wherein a relatively planar, triangular shaped recorder housing 10 is provided with three adhesive electrode pads, 12, 14, and 16 for comfortable attachment to the skin of a patient to be monitored. Although housing 10 is illustrated in the preferred triangular form of a heart, it can be appreciated that housing 10 could be virtually any shaped polygon, triangle, square, rectangle, pentagon, hexagon, . . . , circle, etc. All the hardware and firmware components of the recorder are totally encapsulated in the water proofed housing 10 and are coupled to electrodes on pads 12, 14, and 16, and are mounted on one or more printed circuit boards (PCB) inside housing 10. Housing 10 is designed with a curved circumferential edge to avoid sharp edge injury or irritation of the device with the patient's body. Also for ease and comfortable wearing, housing 10 is preferably constructed of a soft, pliant, lightweight, and rugged material, for example a soft plastic or soft rubber. Alternatively, housing 10 may be constructed of harder materials if necessary for durability and covered with a soft textured material such as Santoprene, manufactured by Advanced Elastomer Systems of Akron, Ohio. After a recording has been made, a Personal Computer (PC) or other data analysis system can be coupled to a data output terminal 20 of recorder housing 10, whereby data can be analyzed and archieved for later use, and the recorder can be cleared, cleaned and mounted on another patient.

Figure 2:
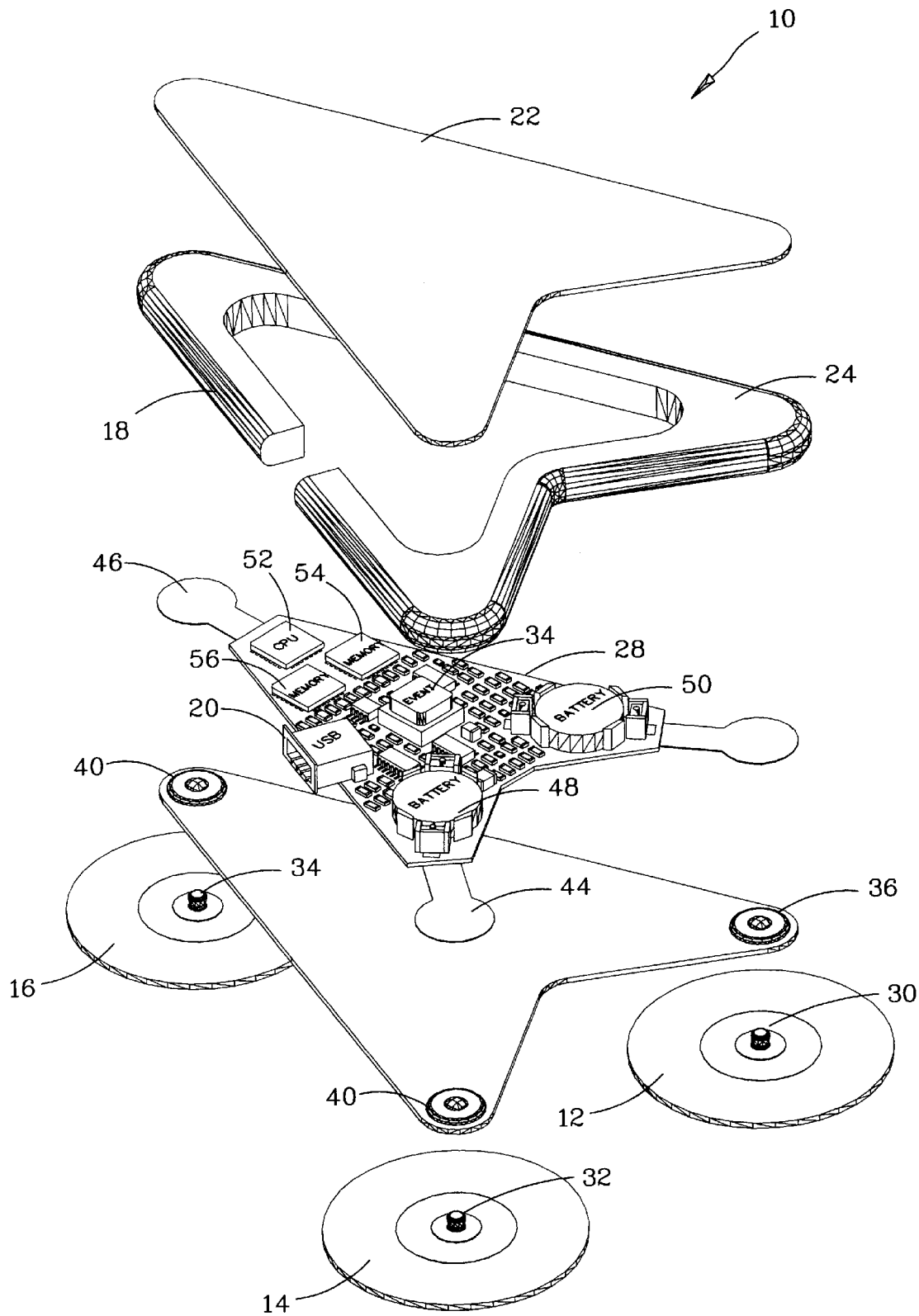
FIG. 2 illustrates an exploded view of FIG. 1.

Referring now to FIG. 2, an exploded perspective view of the physical construction of the ambulatory physiological recorder is illustrated. Housing 10 consists of a planar lid 22 attached by screws, adhesive means or "hook and latch" Velcro means to a peripheral housing wall 24 which, in turn, is attached by similar means to a planar base 26 with a printed circuit board 28 suspended therebetween. Three electrode sensors, a ground sensor 30, a positive sensor 32, and a negative sensor 34 residing in pads 12, 14, and 16, respectively, are insertably clipped into respective conductive receptacles 36, 38 and 40. Conductive arm pads 42, 44, and 46 couple electrodes 30, 32, and 34, respectively, to relevant components on PCB 28.

PCB 28 may consist of two or more parallel PCB's in different embodiments but in all cases performs the function of holding all necessary ambulatory recorder elements. The PCB is powered by one or more removable batteries 48 and 50 and is controlled by a micro processor chip or central processor unit (CPU) 52. Physiological data is recorded in one or more flash memory chips 54 and 56. Once a recording session as been completed, data stored in chips 54 and 56 is passed out through output terminal or universal serial buss (USB) 20 to a typical PC conventionally utilized in data analysis. An event button 58 is also incorporated on PCB 28 to permit the patient to press to document in memory noteworthy or specific "happenings/events" that may occur during the recording process. Event button 58 is positioned immediately under flexible lid 22 and is activated by simply depressing the center of lid 22. Various other electronics, e.g. chips, diodes, transistors, capacitors, inductors, op amps, flip flops, counters, etc., on PCB 28 are conventional in the art and will not therefor be discussed in detail herein.

Figure 3:
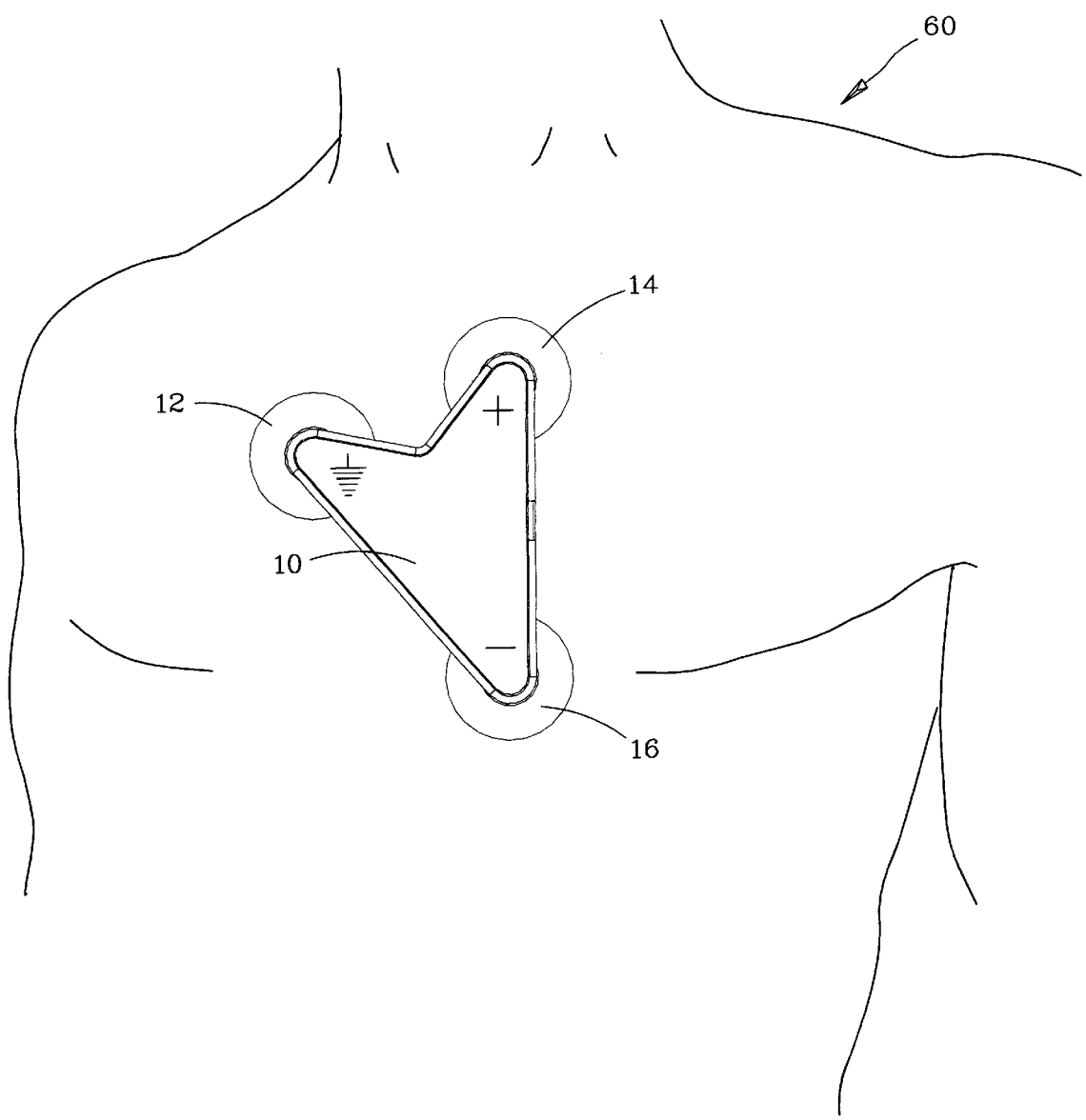
FIG. 3 illustrates the preferred placement of the FIG. 1 ambulatory physiological recorder on the body.

In a long term ambulatory heart monitoring application, i.e. in a "Holter Monitoring" application, the mounting orientation of the first embodiment 10 of the ambulatory physiological recorder is illustrated in FIG. 3. A typical patient body 60 is depicted with recorder 10 flatly disposed thereon. Ground electrode pad 12, positive electrode pad 14, and negative electrode pad 16 are adhesively and conductively attached to the patient's chest in a position generally over the heart wherein the positive and negative terminals are in a relative vertical position from top of the heart to the bottom thereof.

Figure 4:
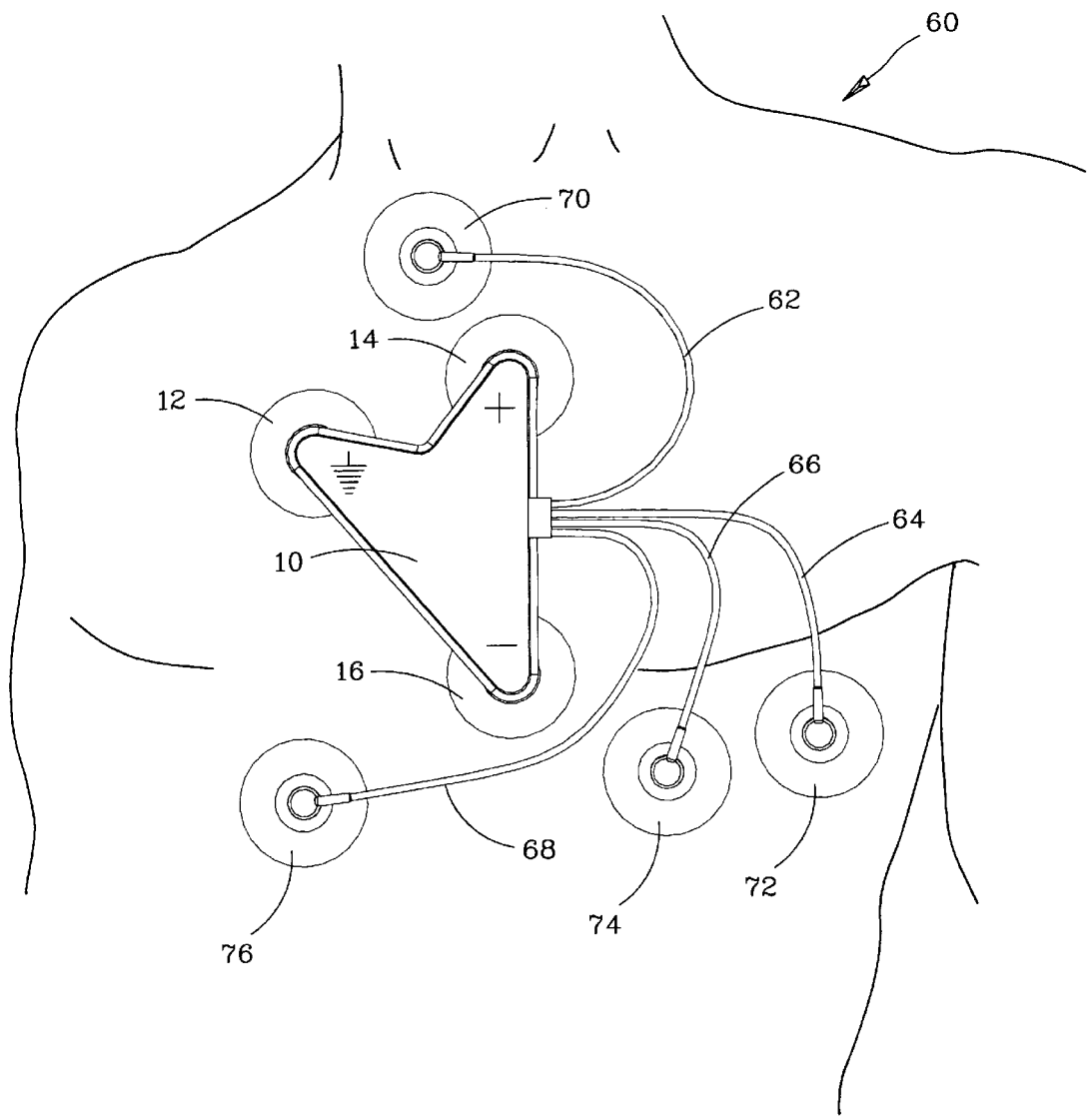
FIG. 4 illustrates the embodiment of FIG. 1 with provision for additional multiple sensor leads.

For physiological monitoring activities other than Holter (heart) Monitoring, or for more slices of the heart in Holter applications, an adaptation of the first embodiment is indicated in FIG. 4, wherein multiple leads 62, 64, 66, and 68 extend from an input port (not illustrated in the Drawing) adjacent to output port 20, to individual peripheral electrodes 70, 72, 74, and 76, respectively. By such means, the fully self contained ambulatory physiological recorder of FIG. 1 is easily expanded to accommodate more information input channels in addition to the built-in electrodes 30, 32, and 34 illustrated in FIG. 2.

Second Embodiment

Figure 5:
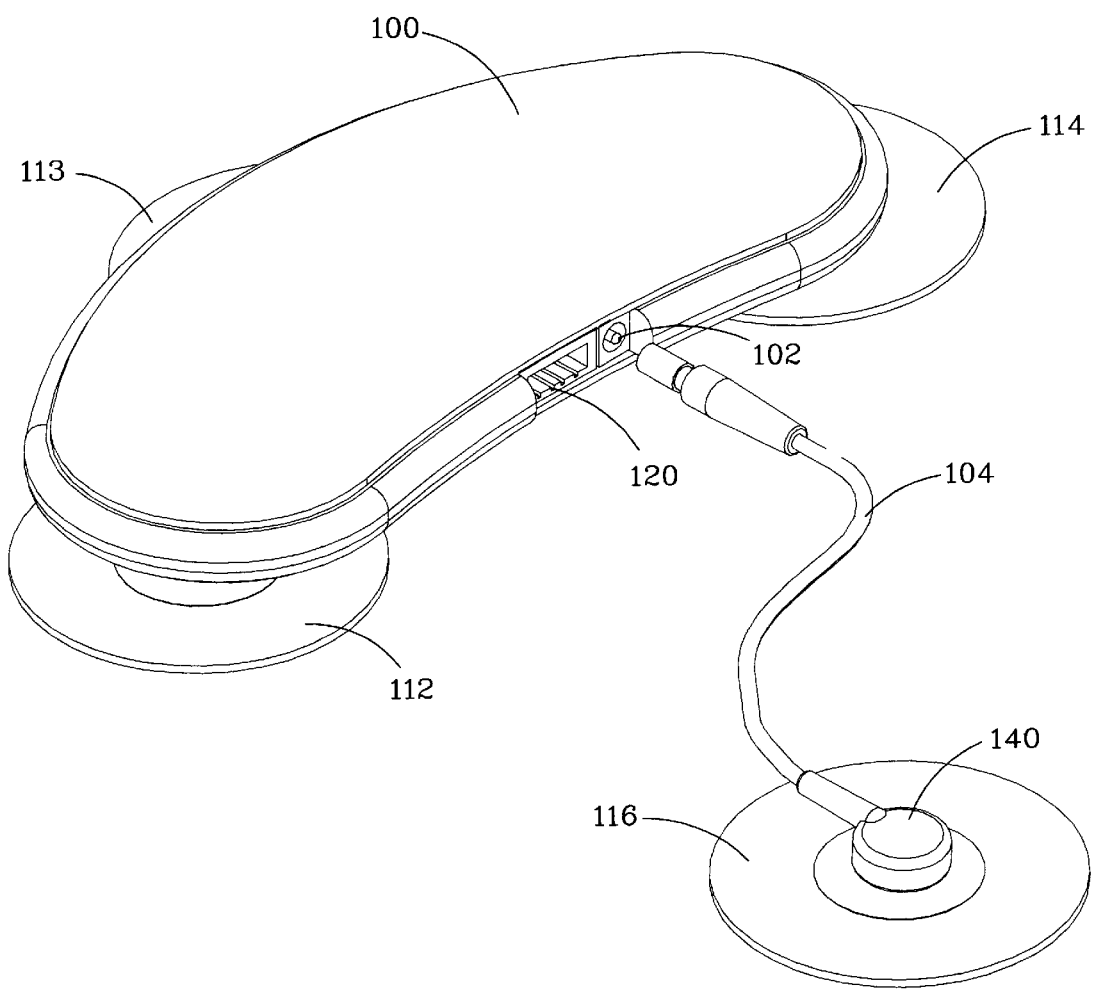
FIG. 5 illustrates a perspective view of a second embodiment of the ambulatory physiological recorder invention.

FIG. 5 illustrates a perspective view of a second embodiment of the invention uniquely designed to adapt to a female torso moreso than a male chest where a woman's breast might interfer with placement of housing 10 and tightly configured terminal pads 12, 14, and 16, and where the size and unavoidable contact of a woman's breasts would necessarily cause a great degree of discomfort, especially when worn for period of time.

As opposed to the triangular/heart shaped recorder housing 10 of the first embodiment of FIG. 1, configured for mounting across the chest and over the heart, the second embodiment of FIG. 5 depicts a kidney or bean shaped recorder housing 100 configured for placement and mounting high on the chest above the breast level, and having essentially the same components as the first embodiment of FIG. 1 with the notable exception that the corresponding negative terminal 134 is not in housing 100 but extends down over the heart and between the breast for ease in wearing the recorder for an extended period of time. The second embodiment of FIG. 5 illustrates a first terminal pad 112, a second terminal pad 113, a third terminal pad 106, and a fourth terminal pad 108. First terminal pad 102 serves as a ground terminal, third terminal pad 114 serves as positive terminal (+), and fourth terminal pad 116 serves as a negative terminal (−). Negative terminal 134 on fourth pad 116 attaches physically and electrically by similar adhesive means as with all other terminal pads and is coupled to housing 100 by and input terminal 102 and coupling lead 104. Terminal pad 113 is not a conducting terminal but serves only as an additional adhesive means, in addition to adhesive terminal pads 112 and 114, to support and maintain the ambulatory recorder on the chest of the patient being monitored. Housing 100, in like manner as with housing 10, provides for output of accumulated data at an output terminal 120 to a conventional PC for conventional analysis, evaluation and archieval of data.

Figure 6:
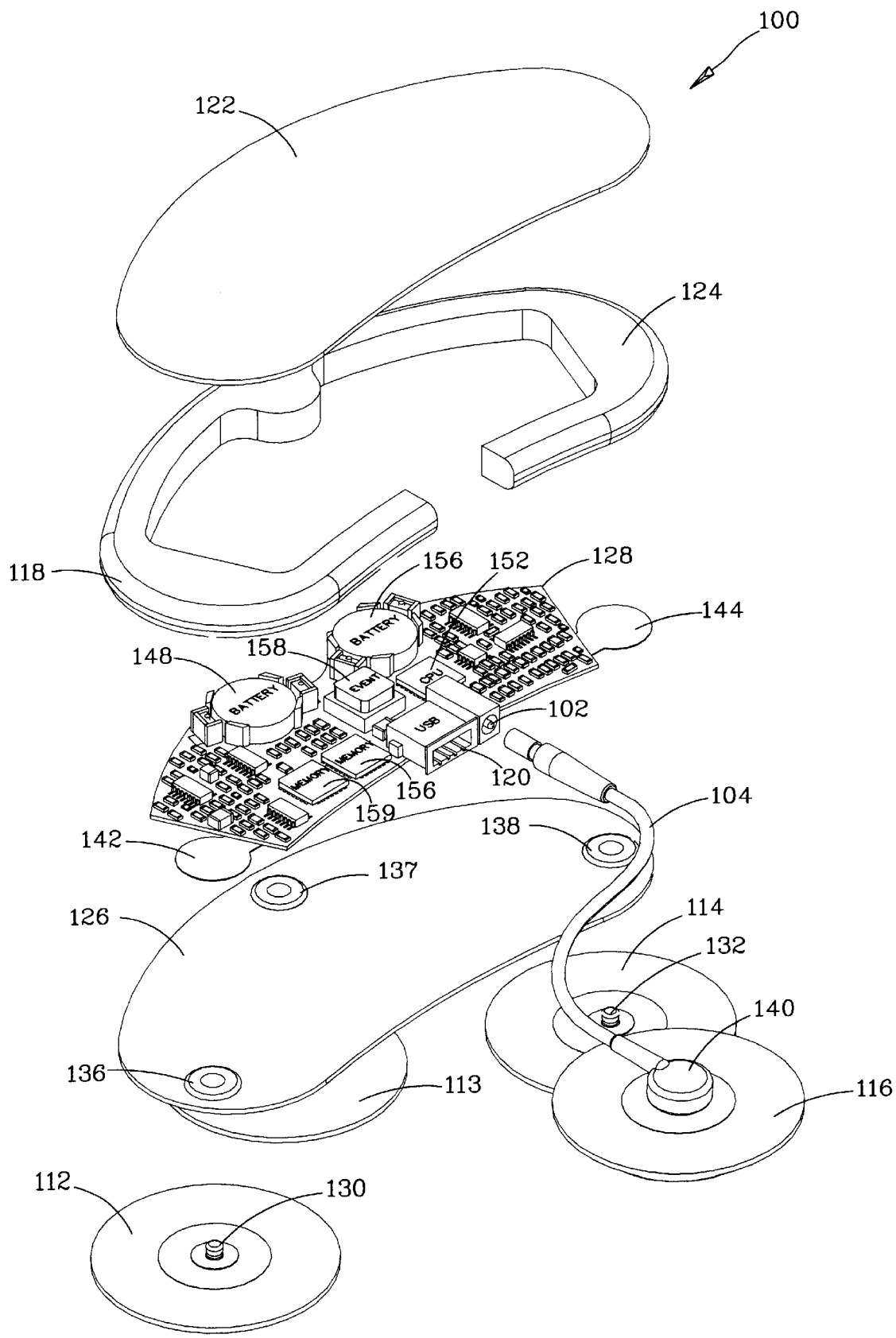
FIG. 6 illustrates an exploded view of FIG. 5.

Referring now to FIG. 6, an exploded, perspective view of the physical construction of the of the second embodiment, ambulatory physiological recorder of FIG. 5 is illustrated. As with the first embodiment, housing 100 consists of a planar lid 122 attached by screws, adhesive means, or hook and latch, Velcro, means to a peripheral housing wall 124, which in turn, is attached by similar means to a planar base 126 with a printed circuit board 128 suspended therebetween. Three electrode sensors, a ground sensor 130, a positive sensor 132, and a negative sensor 134 (hidden) residing in sensor pads 112, 114, and 116, respectively, are insertably snapped into respective conductive receptacles 136, 138, and 140. Conductive arm pads 142 and 144 couple electrodes130 and 132, respectively, to relevant components on PCB 128.

Again, PCB 128 may consist of two or more parallel PCB's in different embodiments but in all cases performs the function of holding all necessary ambulatory recorder elements. PCB 128 is powered by one or more removable batteries 148 and 150 and is controlled by a micro processor chip or central processor unit (CPU) 152. Physiological data is recorded in one or more flash memory chips 154 and 156. Once a recording session as been completed, data stored in chips 154 and 156 is passed out through an output terminal or universal serial buss (USB) 120 to a typical PC conventionally utilized in data analysis. An event button 158 is also incorporated on PCB 128 to permit the patient to press to document in memory noteworthy or specific "happenings/events" that may occur during the recording process. Event button 158 is likewise positioned immediately under flexible lid 122 and is activated by simply depressing the center of lid 122.

Various other electronics, e.g. chips, diodes, transistors, capacitors, inductors, op amps, flip flops, counters, etc. that may be necessary as discrete elements of the PCB in order to perform the long term recording function are conventional in the art and will not therefor be discussed in detail herein.

Figure 7:
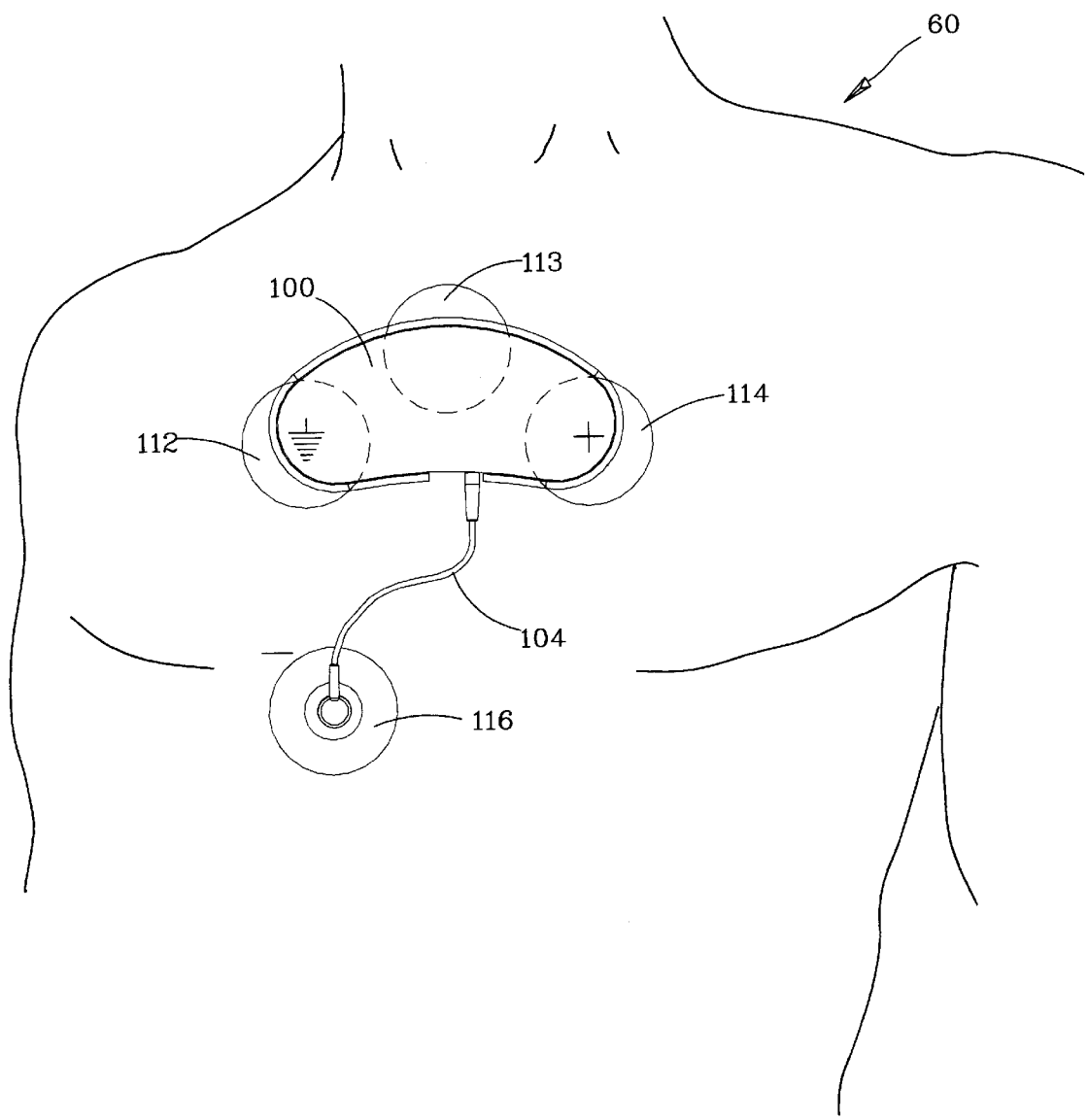
FIG. 7 illustrates the preferred placement of the FIG. 5 ambulatory physiological recorder on the body.

In a long term ambulatory heart monitoring application, i.e. in a "Holter Monitoring" application, the mounting orientation of the second embodiment 100 of the ambulatory physiological recorder is illustrated in FIG. 7. A typical patient body 60 is depicted with recorder 100 flatly disposed thereon. Ground electrode pad 112, positive electrode pad 114, and non conductive electrode pad 113 are adhesively attached to the patient's upper chest in a position generally above the breasts with the negative electrode pad 116 positioned below the breasts coupled via lead 104 to recorder housing 100, wherein the positive and negative terminals are in a relative vertical position from top of the heart to the bottom thereof.

Figure 8:
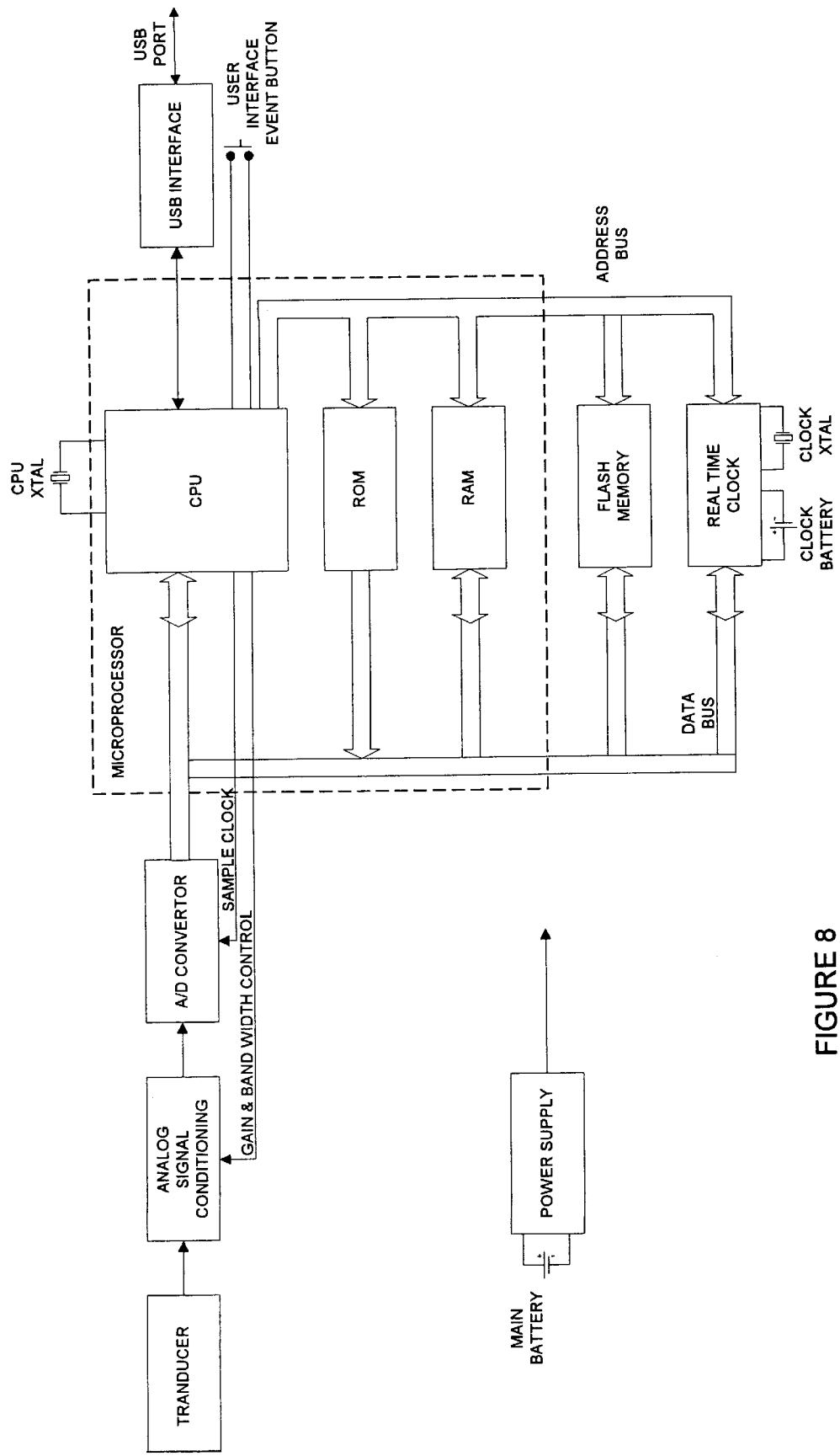
FIG. 8 depicts a block diagram of the printed circuit board and components of the invention.

Referring now to FIG. 8, a block flow diagram of the functional electronic components of PCB's 28 and 128 is delineated. It should be understood that although the external appearance of first and second embodiments of the invention are uniquely different, the PCB components and function thereof are identical. Therefor, only PCB 28 will be addressed in this disclosure for ease of description and understanding. The block flow diagram in FIG. 8 is designed for a very small and compact, lightweight digital recorder. The recorder circuit on PCB 28 in FIG. 8 is designed to accommodate and record a variety of physiological signals. The recorder is specifically designed with the concept to be fully "self contained" and mounted immediately adjacent the organ or system which is to be monitored to, among other reasons, diminish electrical lead artifact and discontinuity; the recorder circuit is powered by an internal battery 200 (elements 48 and 50 of FIG. 2), physically possesses its own attached sensor electrode input devices, data storage, data manipulation (micro processor), and data output. The circuit is designed to operate in an ambulatory environment for a recording period of at least twenty four (24) hours. The transducer, electrode sensor, analog signal conditioning and sampling rate can be changed to meet the requirements of the data to be recorded.

The transducers 202, e.g. electrode sensors 30, 32, and 34, utilized in any particular application will depend on the application of varying bioelectric potentials, such as electrocardiograph (ECG), electroencepholograph (EEG), electromyograph (EMG), etc. Transducer 202 would be appropriate skin contact electrodes such as electrode sensors 30 32, and 34; however, for acceleration, activity or body movement sensors, the transducer would be acceleration sensors; for pressure recording, the transducer would be a pressure transducer; and for skin temperature recording, the transducer would be a thermal type transducer.

Transducer 202 feeds a data signal into an analog signal conditioner 204, the exact elements of which will depend on the transducer type and the recording characteristics desired. These characteristics would include sample rate, resolution, and amount of data to be stored. The signal conditioning function is further characterized by the type of input, the necessary gain, the bandwidth, the signal to noise ratio, the maximum input signal, the maximum output signal, common mode rejection and the operating environment requirement. The primary function of analog signal conditioner 204, however, is to amplify transducer 202 output signal to the level required by an analog to digital converter 206.

Analog to digital converter (A/D) 206 primary function is to sample analog signals on each cycle of a sample clock 208. The A/D output is a digital value represented by one's and zero's on a set of parallel lines. In the preferred embodiment, the typical number of lines or bits would be eight (8). A/D converter 206 is in turn connected by an eight bit data bus 210 to a central processor unit (CPU) 212 within micro processor chip 52.

Central processor unit 212 in the preferred embodiment is a standard CPU used in micro processor and controller environments. CPU 212 function is to read instructions stored in a read only memory (ROM) 214 and to execute those instructions. CPU 212 is the heart of any stored program controller. CPU 212 receives and outputs data through a bidirectional data bus 216 through parallel ports, serial ports and other undefined control pins. An output address buss 218 determines which of the devices connected to data bus 216 is to receive data currently on data bus 216. The address also determines from which device CPU 212 will read data. Other control lines determine weather the data is being determined an output or an input to CPU 212 over data bus 216.

Read only memory (ROM) 214 stores program instructions to control operation of CPU 212. The program instructions stored in ROM 214 is referred to as the embedded program code. Several different programs could be stored in ROM 214. An input by an operator through a universal serial bus port (USB) 220 could determine which one of the programs will be executed. Size of memory 214 will vary with the particular microprocessor used; often in the range of 1 k to 64 k bytes, but typically 16 k bytes in the present application.

Random access memory (RAM) 222 is used by the program executed by CPU 212 for temporary storage of data. Typical use of RAM 222 is as a scratch pad memory, buffer memory and program stack.

Flash memory 224 (elements 54 and 56 of FIG. 2) is a type of nonvolatile memory used in digital devices to store large amounts of data in a small volume. Some of the properties of this type of memory are large volumes of data that can be stored in small chips, e.g. 8 megabytes in a chip 20×12.7 mm. Power can be removed from the device and date will be retained. Data must be written to and read from the memory in blocks of data, typically in 512 byte segments; not a very fast memory.

A built in real time clock 226 makes effective system time and data correlation of data digitized for storage.

Figure 9:
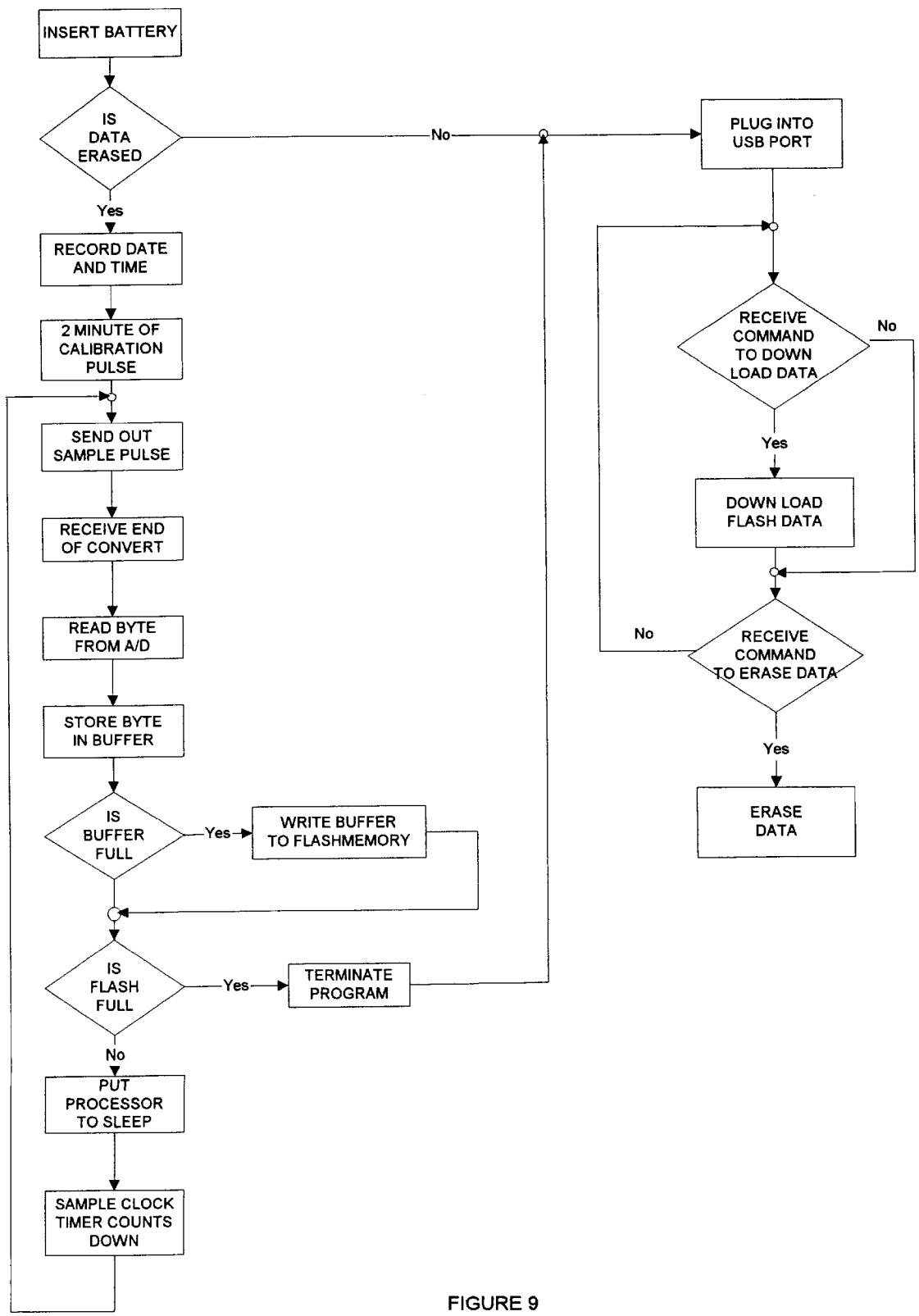
FIG. 9 depicts a block flow diagram of the software recording process of the invention.

Referring now to FIG. 9, a flow chart of the software/firmware operation of the ambulatory physiological recorder (identical for both first and second embodiments) succinctly delineates the logic process for recording data byte by byte. Briefly when the recorder is first powered on and calibrated then mounted onto a patient, data is received from a transducer 202, signal conditioned 204, A/D 206 converted to digital, passes into microprocessor unit 52 to CPU 212 byte by byte to be stored in a temporary buffer until full at which time the accumulated data bytes are passed to flash memory 224 for a predefined recording period. At the end of the recording period or when flash memory is full, data is passed out USB 220 to for example a personal computer (PC) for later analysis and evaluation. The recorder is then physically cleaned and electronically cleaned, data erased, and set up for another patient recording session.

Although the foregoing provides a somewhat detailed description of the invention disclosed, obvious embodiments, alterations and improvements are considered a part of the invention as well. The true scope and extent of the invention concept will be more clearly defined and delineated by the appended claims.

We claim:

1. A flesh/body mounted, self powered, long-term, ambulatory data processor and recorder for accumulation of physiological and somatic data from a patient, comprising:

environmentally sealed recorder housing means for elimination of moisture, dust, and other contaminants from the data processing and recording process;

dual function recorder housing mounting means for adhesively holding said recorder housing in a desired position on the flesh and body of said patient, while concomitantly acting as a data input transducer and physiological sensor of said somatic data; and micro processor system controller means disposed in said recorder housing for receiving, processing, accumulating, recording, and outputting at least one channel of said somatic data;

reusable data storage means disposed in said recorder housing.

2. The recorder housing means according to claim 1, wherein said housing means is soft, flexible, and compliant to body tissue movement.

3. The recorder housing means according to claim 2, wherein said housing means comprises:

a planar lid;

a planar base disposed parallel to said lid, to be placed adjacent the patient body/flesh to which said recorder is to be mounted;

a rounded, circumferential seal and wall disposed around the periphery of and between said lid and base, thereby enclosing a sealed housing environment therebetween; and a printed circuit board extending across said sealed housing environment for supporting said system micro processor, memory, and input/output means.

4. The sealed recorder housing according to claim 3, wherein said base has provision for at least two snap-in receptacles for receipt of at least two snap-on transducer sensor means and adhesive skin attachment means.

5. The recorder housing mounting means according to claim 1, wherein said dual function, transducer/attachment means consists of a snap-on electronic sensor probe surrounded and attached to the patient skin by an adhesive pad.

6. The recorder housing mounting means according to claim 5, wherein said sensor/attachment device is further attached by swivel mount means to said recorder housing, thereby allowing more comfortable and flexible movement of the patient's skin to which said recorder is supported.

7. The ambulatory recorder according to claim 1, wherein said data storage means consists of at least one solid state flash memory chip.

8. The ambulatory recorder according to claim 1, further having data output means consisting of a Universal Serial Bus coupling said micro processor means and data storage means to an exit port of said recorder.

9. The ambulatory recorder according to claim 1, further having data output means in the form of an insertable flash memory card.

10. The ambulatory recorder according to claim 1, wherein said self powered function of said recorder consists of at least one battery disposed within said housing.

11. The ambulatory recorder according to claim 1, further having patient event marking means for indicating time related specific events contiguous to relevant recorded somatic data.

12. The ambulatory recorder according to claim 1, further having the option for data compression for extending periods of recorded data.

13. The ambulatory recorder according to claim 1, further having accelerometer means disposed therein for further data recording capacity of patient physical activity and body movement.

14. Hidden and covert apparatus for monitoring and recording physiological and somatic data from a patient over an extended period and in an ambulatory environment, comprising:

a recorder housing;

means attached to said housing for concomitantly sensing somatic analog signals and also for attaching said recorder housing directly to the patient's body/skin and holding said recorder in place during the recording process;

central processor unit disposed in said housing for receiving, processing, and for converting said somatic signals from analog to digital data; and means for storing said digital data.

15. Covert recording apparatus according to claim 14, wherein said recorder housing is sealed against environmental contaminants to include water.

16. Covert recording apparatus according to claim 15, wherein said recorder housing is constructed of a skin soft, flexible material and capable of bending with the body area over which the recorder is mounted.

17. Recording apparatus according to claim 14, wherein said storing means consists of a solid state, digital, flash memory.

18. Recording apparatus according to claim 14, wherein a microprocessor controller system and other supporting data processing and recording electronics are all mounted on at least one printed circuit board suspended within said recorder housing.

19. Covert apparatus according to claim 14, further having means for a plurality of additional, conventional leads extending from said recorder housing on one part of the body to a variety of other parts of the body.

* * * * *